United States Patent
Amin et al.

(10) Patent No.: US 6,881,407 B2
(45) Date of Patent: Apr. 19, 2005

(54) METHOD FOR TREATING HEPATITIS

(76) Inventors: Ashok Amin, 156 Glenwood Ct., Union, NJ (US) 07083; Steven Abramson, 27 Greenhaven Rd., Rye, NY (US) 10580

( * ) Notice: Subject to any disclaimer, the term of this patent is extended or adjusted under 35 U.S.C. 154(b) by 0 days.

(21) Appl. No.: 09/925,970

(22) Filed: Aug. 10, 2001

(65) Prior Publication Data

US 2002/0037934 A1 Mar. 28, 2002

Related U.S. Application Data

(60) Provisional application No. 60/224,363, filed on Aug. 11, 2000.

(51) Int. Cl.$^7$ ............................................. A61K 39/395
(52) U.S. Cl. ............................... 424/133.1; 424/141.1; 424/143.1
(58) Field of Search .......................... 424/141.1, 133.1, 424/143.1; 514/2

(56) References Cited

U.S. PATENT DOCUMENTS

| | | | |
|---|---|---|---|
| 5,629,285 A | | 5/1997 | Black et al. |
| 5,641,751 A | | 6/1997 | Heavner |
| 5,698,195 A | * | 12/1997 | Le et al. ................... 424/133.1 |
| 5,939,423 A | * | 8/1999 | Karlin et al. .......... 514/263.31 |

FOREIGN PATENT DOCUMENTS

| | | | | |
|---|---|---|---|---|
| WO | WO 98/22137 | * | 5/1998 | ......... A61K/39/395 |

OTHER PUBLICATIONS

Peterson et al. Annals of the Rheumatic Diseases 62(11):1078–1082 (Nov. 2003, not available as prior art). PDF version provided; best available copy is nearly illegible.*

Peterson et al. Annals of the Rheumatic Diseases 62(11):1078–1082 (Nov. 2003, not available as prior art).Full–text version provided from http://gateway.proquest.com/openurl?url_ver=Z39.88– 2004&res_dat= xri:pqd&rft_val_fmt=info:ofi/fmt:kev:mtx:journal&genr.*

Ohta et al, J. Immunol. 165(2): 956–961, 2000.*

Peterson et al., Safety of TNF–$\alpha$ Antagonists in Patients with Rheumatoid Arthritis and Chronic Hepatitis C. Arthritis Rheum. 44(9), Suppl., Nov. 2001, p. S78.*

Tilg et al., Anti–tumor necrosis factor monoclonal antibody therapy in HCV–positive severe alcoholic hepatitis. Hepatology vol. 34, No. 4, Pt. 2, Oct. 2001, p. 696A.*

Hayat et al., Effect of infliximab therapy for rheumatoid arthritis on chronic hepatitis C. Clinical Immunology vol. 103, No. 3, Pa 2, Supp., Jun. 2002, p. S80.*

Biancone et al., Immunomodulatory Drugs in Crohn's Disease Patients With Hepatitis B or C Virus Infection. Gastroenterology vol. 122, No. 2, Feb. 2002, pp. 593–594.*

The Merck Manual of Diagnosis and Therapy, Beers et al., Eds., Seventeenth Edition, published by Merck Research Laboratories, 1999, pp. 384–386.*

Campbell et al., Infliximab therapy for Crohn's disease in the presence of chronic hepatitis C infection. European Journal of Gastroenterology and Hepatology 13(2):191–192, 2001.*

* cited by examiner

*Primary Examiner*—Mary E. Mosher
(74) *Attorney, Agent, or Firm*—Browdy and Neimark, P.L.L.C.

(57) ABSTRACT

Hepatitis can be treated by administering to a patient in need thereof an effective amount of a compound that neutralizes the effects of secreted TNFalpha. Two types of these compounds are extracellular ligand binding proteins of the human p75 TNF receptor, such as etanercept (Enbrel), and humanized monoclonal antibodies that neutralize the activity of TNFalpha, such as inflixamab (Remicade).

5 Claims, No Drawings

METHOD FOR TREATING HEPATITIS

CROSS-REFERENCE TO RELATED APPLICATIONS

The present application claims priority from provisional application Ser. No. 60/224,363 filed Aug. 11, 2000, the entire contents of which are hereby incorporated.

FIELD OF THE INVENTION

The present invention is directed to a method for treating hepatitis.

BACKGROUND OF THE INVENTION

Tumor necrosis factor-alpha (TNF-alpha, also known as cachectin) is a mammalian protein capable of inducing a variety of effects on numerous cell types. TNF-alpha was initially characterized by its ability to cause lysis of tumor cells, and is produced by activated cells such as mononuclear phagocytes, T-cells, B-cells, mast cells and NK cells. Because the deleterious effects which can result from an over-production or an unregulated production of TNF are extremely serious, considerable efforts have been made to control or regulate the serum levels of TNF.

The numerous biological effects of TNF-alpha and the closely related cytokine TNF-beta (lymphotoxin), are mediated by two transmembrane receptors, both of which have been cloned. The 55 receptor, also termed TNF-R55, TNF-RI, or TNFRbeta, is a 55 kd glycoprotein which has been shown to transduce signals resulting in cytotoxic, anti-viral, and proliferative activities of TNF-alpha.

The p75 receptor, also termed TNF-R75, TNF-RII, or TNFRalpha, is a 75 kd glycoprotein that has also been shown to transduce cytotoxic and proliferative signals as well as signals resulting in the secretion of GM-CSF. The extracellular domains of the two receptors are 28% identical in primary structure and have in common a set of four subdomains defined by numerous conserved cysteine residues. The p75 receptor differs, however, by having a region adjacent to the transmembrane domain that is rich in proline residues and contains sites of O-linked glycosylation. The cytoplasmic domains of the two receptors share no apparent homology, which is consistent with observations that they can transduce different signals to the interior of the cell.

There are currently two drugs which have been approved for treatment of rheumatoid arthritis that act by neutralizing the activity of secreted TNF: etanercept (ENBREL), which is based on a p75:pC receptor and a humanized monoclonal antibody that neutralizes the activity of TNF, such infliximab (REMICADE). Etanercept, or ENBREL, is an extracellular ligand binding protein of the human p75 TNF receptor (TNF-R) linked to the Fc portion of human IgG1. Infliximab, or REMICADE, is a humanized monoclonal antibody that neutralizes the activity of secreted TNF. Both ENBREL (Etanercept) and REMICADE (Infliximab) potently bind TNF and block inflammation by inhibiting the downstream effect of this cytokine. ENBREL (Etanercept) can bind to lymphotoxin alpha as well as to TNF.

Hepatitis is an inflammatory disorder which can be caused by viral infections, including Epstein-Barr, cytomegalovirus, and hepatitis A-E viruses. Hepatitis causes acute liver inflammation in the portal and lobular region, followed by fibrosis and tumor progression.

Rheumatoid arthritis is a chronic, progressive and debilitating disease characterized by polyarticular joint inflammation and destruction, with systemic symptoms of fever and malaise and fatigue. Rheumatoid arthritis also leads to chronic synovial inflammation, with frequent progression to articular cartilage and bone destruction.

ENBREL (Etanercept) has been reported to have several side effects, which include possible exacerbation of bacterial infections, including sepsis.

SUMMARY OF THE INVENTION

It is an object of the present invention to provide a treatment for hepatitis.

It is another object of the present invention to treat hepatitis by administering to a patient suffering from hepatitis an effective amount of a compound that neutralizes the activity of secreted TNF.

It is a further object of the present invention to treat hepatitis A–E by administering to a patient suffering therefrom an effective amount of a compound that neutralizes the effect of secreted TNF by inhibiting p75:FC.

It is another object of the present invention to treat hepatitis by administering to a patient suffering from hepatitis an effective amount of a compound that neutralizes the effect of secreted TNF which is a humanized monoclonal antibody.

According to the present invention, compounds that neutralize the effects of secreted TNF not only eliminate the symptoms of rheumatoid arthritis, but also reverse the clinical symptoms associated with hepatitis. Thus, the present invention includes treating a patient suffering from hepatitis with a compound that neutralizes the effects of secreted TNF by inhibiting p75:FC, such as ENBREL (Etanercept) or REMICADE (Infliximab).

DETAILED DESCRIPTION OF THE INVENTION

Hepatitis A–E can to be treated by administering to a patient in need thereof an effective amount of a compound that neutralizes the activity of secreted TNF, such as a ligand binding protein of the human p75 TNF receptor linked to the Fc portion of human IgG1, or a humanized monoclonal antibody that neutralizes the activity of TNF. These types of compounds have been found to reverse evidence of hepatic inflammation, i.e., transaminitis, associated with active hepatitis.

EXAMPLE

A patient was identified with typical symptoms of rheumatoid arthritis, including polyarticular joint swelling and pain. The patient also had evidence of active hepatitis, which was characterized by chronic and persistent elevations of hepatic transaminases (AST, ALT) as well as a marked elevation of serum hepatitis C viral RNA. The patient was treated with various DMARs and NSAIDS for a period of three years, and showed very little signs of relief from rheumatoid arthritis. The patent was then selected for treatment with ENBREL (Etanercept) at 25 mg. twice weekly.

The rheumatoid arthritis symptoms prior to treatment included active synovitis in multiple joints (MCR, PLP, wrist, knees). The hepatitis symptoms prior to treatment included hepatitis C viral RNA of 985,000 units and abnormal liver enzymes of four years.

The patient was administered 25 mg. of ENBREL (Etanercept), an extracellular ligand binding protein of the human p75 TNF receptor linked to the Fc portion of human IgG1, twice weekly for five weeks. After five weeks of treatment with ENBREL (Etanercept), the rheumatoid arthritis showed 20–30% symptomatic improvement. The hepatitis symptoms after treatment included viral RNA of 165,000 units and a normalization of liver enzymes, including aspartate transaminase and alanine transaminase, on repeated testing after five weeks of treatment with ENBREL (Etanercept).

TNF neutralizing compounds were found not only to eliminate the symptoms of rheumatoid arthritis as seen in the majority of patients, but were found also to reverse the clinical symptoms associated with hepatitis, including normalization of liver enzymes and decrease in serum viral levels. These anti-inflammatory compounds demonstrate the involvement of TNF alpha in viral diseases such as hepatitis where viral infection and inflammation are closely associated. In addition to reducing inflammation, this therapy appears also to boost the immune system to reduce the viral load by 80% during a chronic infection. Therefore, anti-TNF-alpha therapy can be used for treating hepatitis-induced tumors and other viral diseases.

For treatment of hepatitis, the compounds that neutralize the activity of secreted TNF can be administered by any means and in any amount that achieves the intended propose. Amounts and regimens of a compound that neutralizes the activity of secreted TNF can be determined readily by those with ordinary skill in the art of treating diseases mediated by TNF. Generally, the compounds that neutralize the activity of secreted TNF can be administered in amounts of from about 5 mg to about 125 mg once to seven times weekly. The compounds are administered until the patient exhibits no signs of abnormal liver enzymes.

For example, administration can to be by parenteral, such as by the subcutaneous, intravenous, intramuscular, intraperitoneal, transdermal, or buccal routes. Alternatively or concurrently, administration can be by the oral route, transdermally, tranmucosally, or rectally. The dosage administered depends upon the age, health, and weight of the recipient, type of treatment, frequency of the treatment, and the nature of the effect desired.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus, the expressions "means to . . . " and "means for . . . ", or any method step language, as may be found in the specification above and/or in the claims below, followed by a functional statement, are intended to define and cover whatever structural, physical, chemical, or electrical element or structure, or whatever method step, which may now or in the future exist which carries out the recited functions, whether or not precisely equivalent to the embodiment or embodiments disclosed in the specification above, i.e., other means or steps for carrying out the same function can be used; and it is intended that such expressions be given their broadest interpretation.

What is claimed is:

1. A method for treating hepatitis C comprising administering to a patient in need thereof an effective amount of etanercept.

2. A method for treating hepatitis C comprising administering to a patient in need thereof an effective amount of infliximab.

3. A method for treating hepatitis C comprising administering to a patient in need thereof an effective amount of a compound that reduces viral levels in the patient wherein the compound that reduces viral levels is selected from the group consisting of infliximab and etanercept.

4. The method according to claim 3 wherein the compound is etanercept.

5. The method according to claim 3 wherein the compound is infliximab.

* * * * *